US00PP36569P2

(12) United States Plant Patent
Williams

(10) Patent No.: US PP36,569 P2
(45) Date of Patent: Mar. 25, 2025

(54) ***COLOCASIA* PLANT NAMED 'FLOCOCLEO'**

(50) Latin Name: ***Colocasia esculenta* (L.) Schott**
Varietal Denomination: FLOCOCLEO

(71) Applicant: Brian's Botanicals, Louisville, KY (US)

(72) Inventor: Brian Paul Williams, Louisville, KY (US)

(73) Assignee: Brian's Botanicals, Louisville, KY (US)

( * ) Notice: Subject to any disclaimer, the term of this patent is extended or adjusted under 35 U.S.C. 154(b) by 0 days.

(21) Appl. No.: 18/831,287

(22) Filed: Oct. 17, 2024

(30) Foreign Application Priority Data

Oct. 17, 2024 (QZ) ..... PBR 2023/2199

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP28,766 P2 * 12/2017 Williams ..... A01H 6/10
Plt./373

* cited by examiner

*Primary Examiner* — Karen M Redden
(74) *Attorney, Agent, or Firm* — Samuel R. McCoy, Jr.

(57) ABSTRACT

'FLOCOCLEO' is a distinctive *Colocasia* plant which is characterized by the combination of a unique coloration pattern on the lamina of greyed-purple, purple, and violet midrib, a dark purple petiole, glossy concave cordate leaves, and the consistency of these characteristics from generation to generation.

3 Drawing Sheets

Latin name of the genus and species: The Latin name of the genus and species of the novel variety disclosed herein is *Colocasia esculenta* (L.) Schott.

Variety denomination: The inventive variety of *Colocasia* disclosed herein has been given the variety denomination 'FLOCOCLEO'.

CROSS REFERENCE TO RELATED APPLICATIONS

This application claims priority to the Community Plant Variety Rights application number 2019/2199, filed Oct. 17, 2023, which is herein incorporated by reference.

BACKGROUND OF THE INVENTION

Parentage: 'FLOCOCLEO' is the product of a controlled breeding program carried out in 2016 at a plant nursery in Louisville, Kentucky using *Colocasia esculenta* 'Pink China Hybrid 2013' (unreleased and unpatented) as the seed parent and *Colocasia esculenta* 'Nancyana Hybrid 2012' (unreleased and unpatented) as the pollen parent. The new plant was first observed in August of 2018 and was noted for its unique, colorful foliage and improved cold hardiness relative to other progenies from said cross. *Colocasia esculenta* 'FLOCOCLEO' was subsequently isolated for further evaluation to confirm the distinctness and stability of the characteristics first observed. Upon confirmation of distinctness and stability, 'FLOCOCLEO' was selected for commercialization in August of 2021.

Asexual Reproduction: Asexual reproduction of 'FLOCOCLEO', by way of meristematic tissue culture, was first initiated in April of 2023 at a plant tissue culture laboratory in Nootdorp, The Netherlands. Through several subsequent generations of propagation there have been more than one thousand progenies produced which all maintain the unique features of the new plant.

SUMMARY OF THE INVENTION

The cultivar 'FLOCOCLEO' has not been observed under all possible environmental conditions. The phenotype may vary somewhat with variations in environment such as temperature, water availability, and light intensity, without, however, any variance in genotype. The following traits have been repeatedly observed and are determined to be the unique characteristics of 'FLOCOCLEO'. These characteristics in combination distinguish 'FLOCOCLEO' as a new and distinct *Colocasia* cultivar:

1. *Colocasia* 'FLOCOCLEO' exhibits a unique coloration on the lamina near the point of union with the petiole that is a blend of greyed-purple, purple, and violet; and
2. *Colocasia* 'FLOCOCLEO' exhibits glossy cordate leaves that are carinate and strongly rugose on the abaxial surface; and
3. *Colocasia* 'FLOCOCLEO' exhibits a greyed-purple to purple color combination on the abaxial surface venation and petiole.

BOTANICAL DESCRIPTION OF THE PLANT

Figure 1:
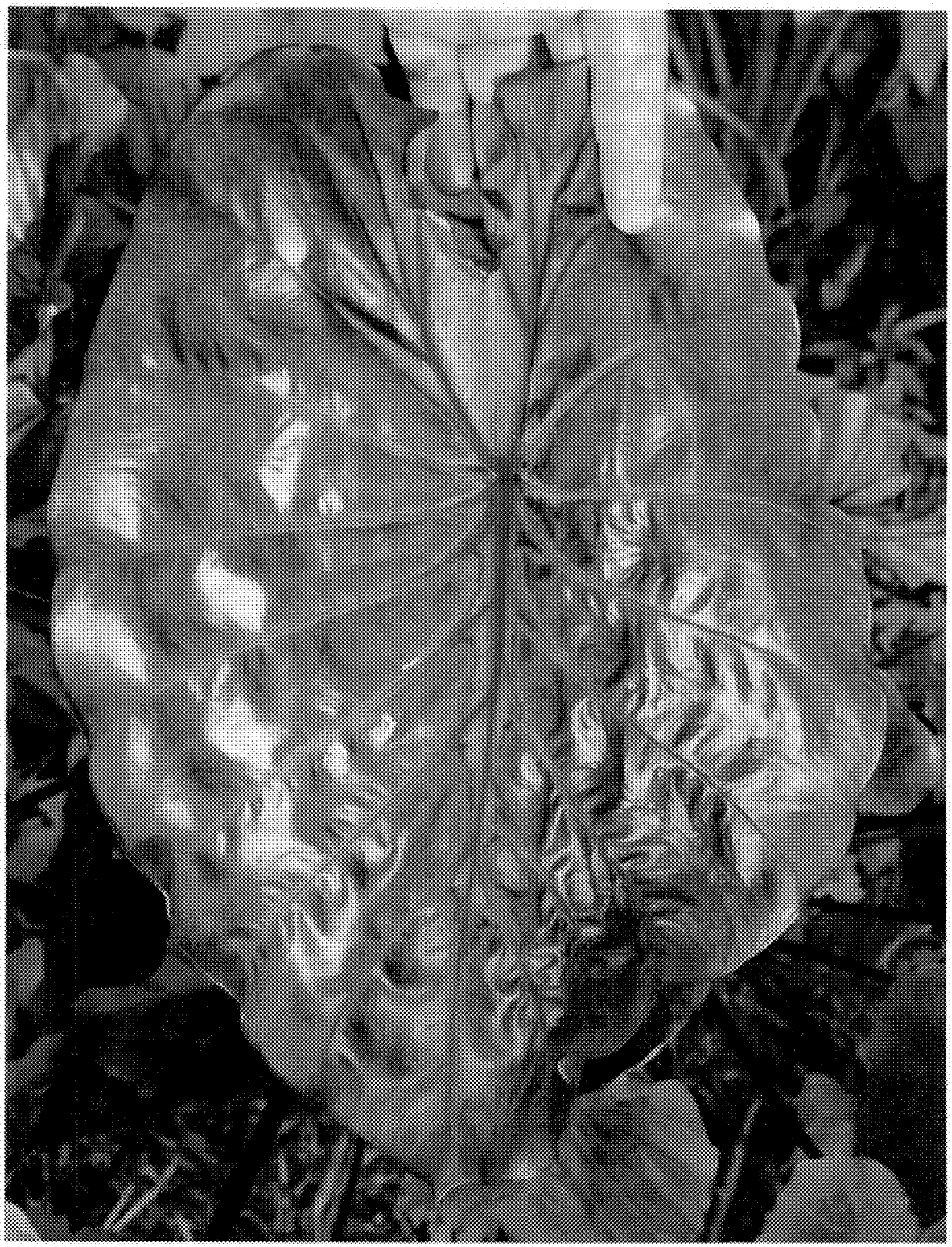
FIG. 1 illustrates, as nearly true as it is reasonably possible to make the same in color photographs of this type, the adaxial surface of a mature 'FLOCOCLEO' lamina. This plant was grown in a commercial greenhouse in Gavenzande, the Netherlands and are approximately 9 months old.
Figure 2:
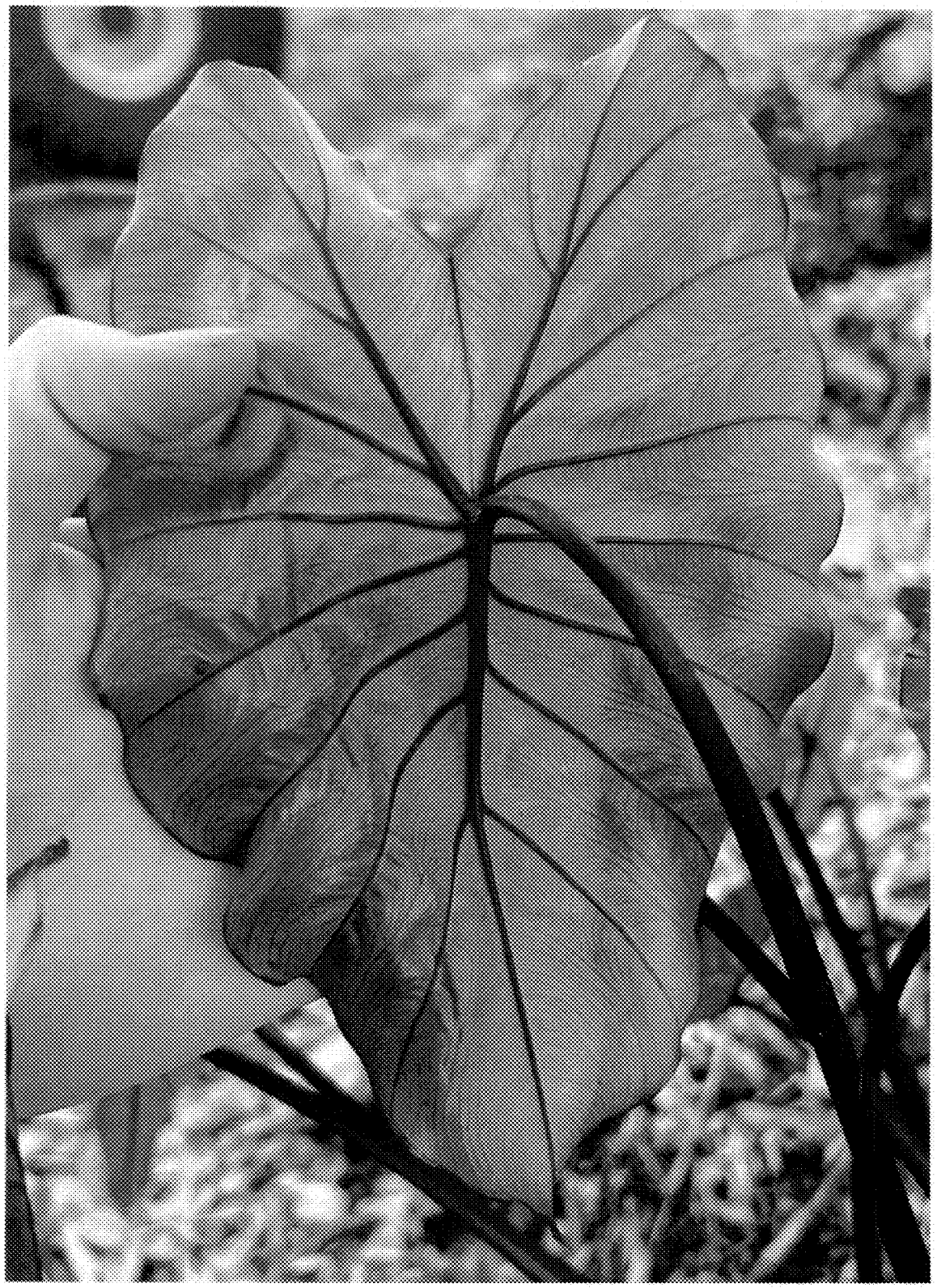
FIG. 2 illustrates, as nearly true as it is reasonably possible to make the same in color photographs of this type, the abaxial surface of a mature 'FLOCOCLEO' lamina.
Figure 3:
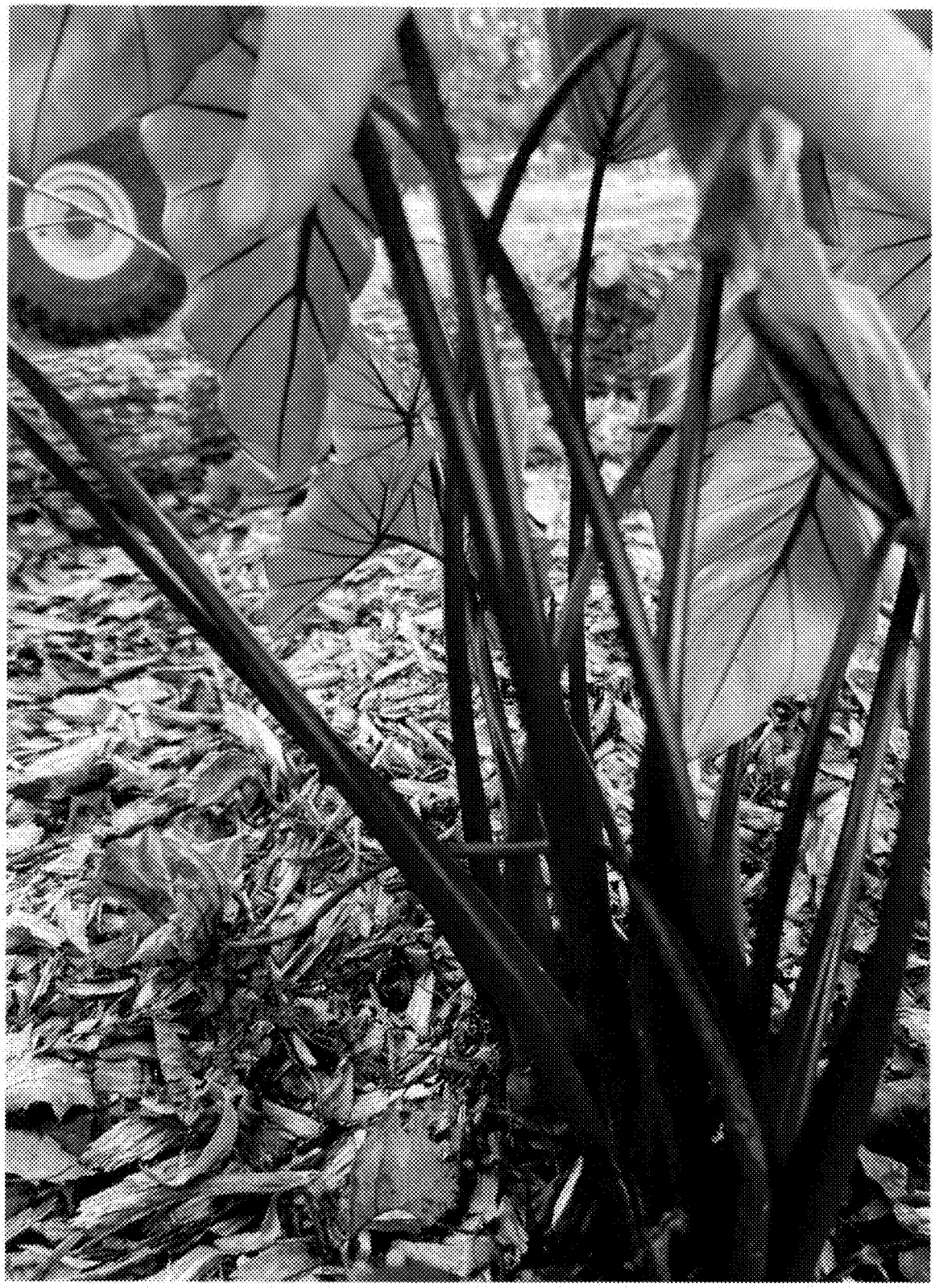
FIG. 3 illustrates, as nearly true as it is reasonably possible to make the same in color photographs of this type, the typical petiole of 'FLOCOCLEO'.

The following observations and measurements made in October of 2024 describe the approximations of a 'FLOCOCLEO' plant grown in a 25 cm nursery container at a greenhouse in South Carolina, United States. The plant was produced in a climate-controlled greenhouse with 35 percent shade covering and was maintained with regular overhead irrigation, slow-release granular fertilizer with a complete analysis, curative chemical pest control measures to control aphids and spider mites, and preventative fungicide applications.

This unique plant exhibits variations in its appearance that may be appreciated as the plant goes through its developmental stages. 'FLOCOCLEO' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, Second Edition.

A botanical description of 'FLOCOCLEO' and a comparison with the parent plants and most similar commercial comparator are provided below.

Plant description:

*Growth habit*.—Clumping herbaceous perennial with a broad, upright growth habit; Acaulescent, leaves growing from a basal clump.

*General plant profile*.—Broad obovate.

*Height from soil level to top of foliar plane*.—Approximately 185.0 cm.

*Plant spread*.—Approximately 125.0 cm.

*Growth rate*.—Moderate.

*Plant vigor*.—Moderately vigorous.

*Propagation type*.—Meristematic tissue culture.

*Time to produce a rooted cutting*.—On average 2 to 3 weeks to produce a rooted cutting at approximately 25 degrees Celsius.

*Time to produce a finished plant*.—On average 3 to 5 weeks to produce a marketable finished plant in a 12 to 17 cm pot.

*Disease and pest resistance or susceptibility*.—Neither susceptibility nor resistance to pests and diseases common to *Colocasia* have been observed.

*Environmental tolerances*.—Adapt to temperatures as low as 5 degrees Celsius and as high as 40 degrees Celsius; moderate to high tolerance to rain; low tolerance to wind.

Foliage:

*Quantity of leaves per shoot*.—12.

*Arrangement*.—Basal foliage is alternate to spiraled.

*Attachment*.—Petiolate.

*Division*.—Simple.

*Lamina*.—Attitude — Ranging from near horizontal to slightly pendulous. Shape — Narrow cordate. Length — approximately 60.0 cm, excluding the petiole. Width — approximately 45.0 cm. Apex — Acuminate. Base — Cordate; lobes free. Aspect — Concave. Attitude — The lamina is at a 90-degree angle from the petiole at the point of attachment; hanging pendulously. Margins — Entire; strongly undulated. Texture and luster, adaxial surface — Strongly rugose, coriaceous, glabrous, glossy, and strongly to moderately glaucous. Texture and luster, abaxial surface — Strongly rugose, coriaceous, glabrous, glossy, and strongly to moderately glaucous Color — Juvenile foliage, adaxial surface — Beginning at the junction point of where the lamina and the petiole connect, the coloration is greyed-purple, nearest to 186A; with undertones of greyed-yellow, nearest to 160D. The lamina gradually becomes greener as the color feathers out towards the margins seen as a green to yellow-green combination of 137A and 147A. Juvenile foliage, abaxial surface — At the point where the lamina and the petiole connect, the coloration is greyed-purple, nearest to 186A; with undertones of greyed-yellow, nearest to 160D. The lamina gradually becomes greener away from the midrib and attachment point of the petiole as a combination of green 137A and yellow-green 147A. Mature foliage, adaxial surface — Beginning in the midrib at the union of the lamina and petiole, and along the lateral veins, the coloration has undertones of greyed-yellow nearest to 160D which is suffused with greyed-purple 186A; As the lamina continues the color begins fading into a blend of yellow-greens, nearest to 144A and 147A. Mature foliage, abaxial surface — The bottom of the lamina shows the same blend of yellow-greens as the upper portion, nearest to 144A and 147A. Venation — Pattern — Pinnate. Color, adaxial surfaces — Lateral veins are a mix of greyed-purple and violet, nearest to a combination of 186B and 87C turning into a darker purple, nearest to 79A, towards the midrib and where the lamina attaches to the petiole. Color, abaxial surface — Greyed-purple, closest to a combination of 187A and 187B with suffusion of purple, nearest to 79A.

*Petiole*.—Attitude — Outward pendulous. Aspect — Terete. Strength — Very strong. Length — Approximately 85.0 cm. Width — 2.5 cm, proximally to base of the petiole, and 0.4 cm at the distal end. Texture and luster — Smooth, glabrous and glaucous. Color — Greyed-purple, closest to a combination of 187A and 187B with suffusion of purple, nearest to 79A. Petiole wings — General description — Two petiole wings extend to about one-third of the length of the petiole, wings attached. Length — Approximately 25.0 cm. Width — Approximately 5.0 cm. Margin — Entire; not undulated. Texture and luster — Smooth, glabrous, glaucous and glossy. Color — Greyed-purple, closest to a combination of 187A and 187B with suffusion of purple, nearest to 79A.

Inflorescence: *Colocasia* typically produces a spathe and spadix inflorescence, but no flowering has been observed to date.

COMPARISONS WITH THE PARENT PLANTS

Plants of the new cultivar 'FLOCOCLEO' differ from the seed parent, an unpatented *Colocasia esculenta* plant (Pink China hybrid 2013), in the characteristics described in Table 1 below.

TABLE 1

| Characteristic | 'FLOCOCLEO' | The seed parent |
|---|---|---|
| General coloration of the petioles. | Greyed-purple to purple petioles. | Light pink petioles. |
| General coloration of the mature foliage. | A blend of darker yellow-greens with a central zone that is colored greyed-purple, generally appearing as dark pink. | Light green with a small pink blotch in the central zone of the lamina. |
| Texture and luster. | Strongly rugose with a glossy shine. | Non rugose with a matte finish. |

Plants of the new cultivar 'FLOCOCLEO' differ from the parent, an unpatented *Colocasia esculenta* 'Nancyana Hybrid 2012', in the characteristics described in Table 2 below.

TABLE 2

| Characteristic | 'FLOCOCLEO' | 'Nancyana Hybrid 2012' |
|---|---|---|
| General coloration of the petioles. | Greyed-purple to purple petioles. | Light green. |

TABLE 2-continued

| Characteristic | 'FLOCOCLEO' | 'Nancyana Hybrid 2012' |
|---|---|---|
| General coloration of the mature foliage. | A blend of darker yellow-greens with a central zone that is colored greyed-purple, generally appearing as dark pink. | Green with a white coloration in the central zone of the lamina. |

COMPARISONS WITH THE CLOSEST KNOWN COMPARATOR

Plants of the new cultivar 'FLOCOCLEO' differ from the closest known commercial comparator, *Colocasia zebrina* 'Black Magic' (not patented), in the following characteristics described in Table 3 below.

TABLE 3

| Characteristic | 'FLOCOCLEO' | 'Black Magic' |
|---|---|---|
| Foliage color. | A blend of darker yellow-greens with a central zone that is colored greyed-purple, generally appearing as dark pink. | Dark black foliage. |
| Color of petioles. | Greyed-purple to purple petioles. | Dark maroon. |
| Foliage texture and luster. | Strongly rugose with a glossy shine. | Non-rugose with a matte finish. |

That which is claimed is:

1. A new and distinct variety of *Colocasia* plant named 'FLOCOCLEO', substantially as described and illustrated herein.

* * * * *